United States Patent [19]

Flournoy

[11] 4,418,574

[45] Dec. 6, 1983

[54] MAGNETIC METHOD AND APPARATUS FOR MEASURING WALL THICKNESS

[75] Inventor: Norman E. Flournoy, Houston, N.Y.

[73] Assignee: Texaco Inc., White Plains, N.Y.

[21] Appl. No.: 323,600

[22] Filed: Nov. 20, 1981

[51] Int. Cl.³ ..................... G01N 29/04; G01N 27/82
[52] U.S. Cl. ..................... 73/601; 324/220; 324/226; 324/229
[58] Field of Search ........... 73/601; 324/219, 226, 324/220, 221, 229

[56] References Cited

U.S. PATENT DOCUMENTS

| | | | |
|---|---|---|---|
| 2,573,799 | 11/1951 | Machean | 324/219 |
| 3,205,435 | 9/1965 | Nuttall | 324/220 |
| 3,237,446 | 3/1966 | Wood | 73/601 |
| 3,356,938 | 12/1967 | Wood | 324/221 |
| 3,732,726 | 5/1973 | Ferber | 73/601 |
| 3,764,897 | 10/1973 | Greenwood | 324/229 |
| 4,292,588 | 9/1981 | Smith | 324/229 |

*Primary Examiner*—Howard A. Birmiel
*Attorney, Agent, or Firm*—Carl G. Ries; Robert A. Kulason; Henry C. Dearborn

[57] ABSTRACT

A pulsed magnetic procedure and apparatus for measuring wall thickness. It is especially applicable to pipelines. It includes pulsing a magnetic reluctance coil that is located close to the wall, and measuring the inductance of the pulsed coil. Also the distance of the coil from the wall is accurately determined so that the inductance is a measure of the wall thickness.

Apparatus may include the combination of an ultrasonic transducer mounted fixed relative to the magnetic pulse coil and arranged so that ultrasonic energy pulses are directed toward the wall. In this manner reflected ultrasonic pulses will provide a measure of the distance. In addition, by proper angle thereof, ultrasonic pulses may also determine the presence of any anomaly.

5 Claims, 7 Drawing Figures

MAGNETIC METHOD AND APPARATUS FOR MEASURING WALL THICKNESS

BACKGROUND OF THE INVENTION

1. Field of the Invention

This invention concerns wall thickness measurements in general. More specifically it concerns a method and apparatus for measuring wall thickness of metallic material. It is also well adapted for making combined measurements of wall conditions in pipelines and the like.

2. Description of the Prior Art

Magnetic methods have been used heretofore for finding anomalies of pipes or pipelines. But, they have not been found quantitatively accurate, and they often fail to provide a true qualitative representation of accurate wall conditions. It has been found that magnetic permeability differences between the steel pipe and surrounding medium, become a primary problem when sensor pads bounce and vibrate from the pipe wall as a result of passing weld joints and other obstructions. Also, magnetic fields induced into the pipe by current conducting brushes or permanent magnets are often unstable.

Consequently, it is an object of this invention to provide a method for measuring wall thickness of metallic materials which method uses a pulsed magnetic reluctance coil rather than passive sensor coils or diodes in the presence of a steady state magnetic field. In addition, this method provides for determining the distance between such pulsed coil and the metallic material in order that the inductance measured may be compensated to provide accurate indication of wall thickness.

SUMMARY OF THE INVENTION

Briefly, the invention concerns a magnetic method for measuring wall thickness of metallic material which comprises the steps of applying a pulse of energy to a magnetic reluctance coil having said metallic material in the proximity of said coil, and measuring the inductance of said pulsed coil. It also comprises determining the distance between said pulsed coil and said metallic material, whereby said inductance is a measure of said wall thickness.

Again briefly, the invention relates to a pipeline wall condition monitor. And, it concerns a magnetic method for finding anomalies. The method comprises applying a pulsed magnetic field to said pipeline wall, and measuring the permeability of the magnetic circuit of said field. It also comprises measuring the length of the flux path of said magnetic circuit.

Again briefly, the invention concerns a pipeline wall condition monitor which comprises in combination, means for magnetically pulsing said pipeline wall to measure the permeability thereof, and means for determining the distance of said pulsing means from said wall in order to correct for variations thereof.

Again briefly, the invention concerns a combined magnetic and acoustic wall thickness and condition measuring apparatus. It comprises in combination a pulsed magnetic reluctance means for measuring said wall thickness, and ultrasonic means for measuring the distance of said magnetic means from said wall.

Once more briefly, the invention concerns a combined magnetic and acoustic wall thickness and condition measuring apparatus. It comprises in combination a reluctance coil having the axis thereof transverse to said wall and adapted for having a small gap between the coil and said wall in order to include said wall in the magnetic field of the coil. And, it comprises first circuit means for pulsing said reluctance coil and for determining the permeability of said magnetic circuit. It also comprises an ultrasonic transducer mounted in a fixed position relative to said reluctance coil, and acoustic reflecting means for directing ultrasonic energy both perpendicular to said wall and at an angle of incidence greater than the critical angle of refraction of said wall. It also comprises second circuit means for pulsing said transducer and for measuring reflected ultrasonic energy from both said perpendicular and angled energy paths.

BRIEF DESCRIPTION OF THE DRAWINGS

The foregoing and other objects and benefits of the invention will be more fully set forth below in connection with the best mode contemplated by the inventor of carrying out the invention and in connection with which there are illustrations provided in the drawings, wherein.

DESCRIPTION OF THE PREFERRED EMBODIMENTS

Figure 1:
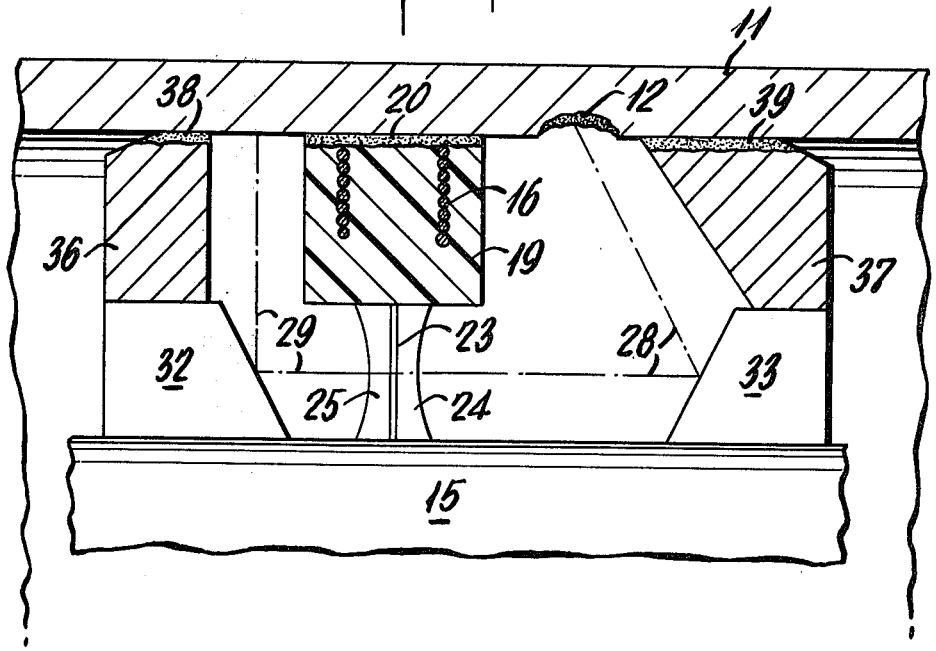
FIG. 1 is a schematic cross-sectional showing which illustrates apparatus according to the invention as it would be used for making measurements in a pipe.

FIG. 1 is a schematic indication of the elements used in an acoustic wall thickness and condition measuring apparatus that is combined with a magnetic measurement. It will be appreciated that apparatus according to this invention could be employed for detecting and identifying pits which might be external or internal relative to the pipe of a pipeline, an offshore platform riser, a storage tank bottom or any other inaccessible steel or iron structure. Also, as will appear more fully hereafter, this inspection device could be used as a single unit or in multiples (not shown), depending upon the area and configuration of the structure that is to be inspected.

For a pipeline instrument, multiple units or devices would be arranged around the periphery of the pipe in order to allow electronic stepping from one device to another so as to cover the entire wall of the pipe. Such an arrangement of the units would be similar to that indicated in a patent assigned to the same assignee as this application; i.e. U.S. Pat. No. 4,022,055 issued May 10, 1977.

With reference to FIG. 1, there is a pipe wall 11 which has an internal pit 12 that may have been caused by corrosion or the like, and the presence of which is to be determined.

An instrument 15 is schematically shown. It has mounted thereon a reluctance coil 16 that may be mounted in a block of supporting material 19 in a manner such that the axis of coil 16 is transverse to the wall 11 of the pipe. Also, there may be a thin surface of wear-resistant material 20 which bears against the inside surface of the pipe 11 as the instrument is used when surveying pipe wall conditions.

Mounted in a fixed position relative to the reluctance coil 16, there is an ultrasonic transducer 23 that has acoustic material lenses 24 and 25 one on each face of transducer 23 in order to focus the acoustic energy pulses. Such pulses are generated by the transducer 23 when it is electrically pulsed in a manner that is known to those skilled in the art, e.g. as generally described in the above mentioned U.S. Pat. No. 4,022,055. The acoustic pulses are focused into columnar form for transmitting them along the identical paths (shown by dashed lines) 28 and 29, respectively.

Also mounted on the instrument 15 there are a pair of acoustic reflectors 32 and 33 that have the reflecting surfaces of each set at desired angles so that the column 29 of acoustic energy will be reflected at a right angle or transverse path relative to the pipe wall 11. And, the reflecting surface of the reflector 33 has an angle such that its column of acoustic energy (path 28) will be directed at an angle of incidence relative to the pipewall 11 which is greater than the critical angle of refraction of the wall. This provides for operating conditions similar to those described in the above noted U.S. Pat. No. 4,022,055 so that any reflected acoustic energy will indicate the presence of a pit or other anomaly such as the pit 12. Such reflected acoustic energy returns along the acoustic path 28 indicated, and generates a signal at the transducer 23 which indicates the presence of the anomaly. In the absence of such anomaly no reflected acoustic energy will return because of the angle of incidence indicated.

At the other face of the transducer 23, the acoustic energy pulses are transmitted so as to reflect from the reflector 32 and be directed at right angles to the surface of the pipe 11. Consequently, there will be reflected energy returned from both the inside and from the outside of the pipe wall 11. Such acoustic signals will then provide a measure of the thickness of the wall 11 as well as a measure of the distance from the instrument to the inside surface of the pipe wall 11.

It will be understood that the instrument 15 includes portions 36 and 37 thereof which each have a wear-resistant surface layer 38 and 39, respectively. These surface layers bear against the inside surface of the wall 11 during normal operations.

Figure 2:
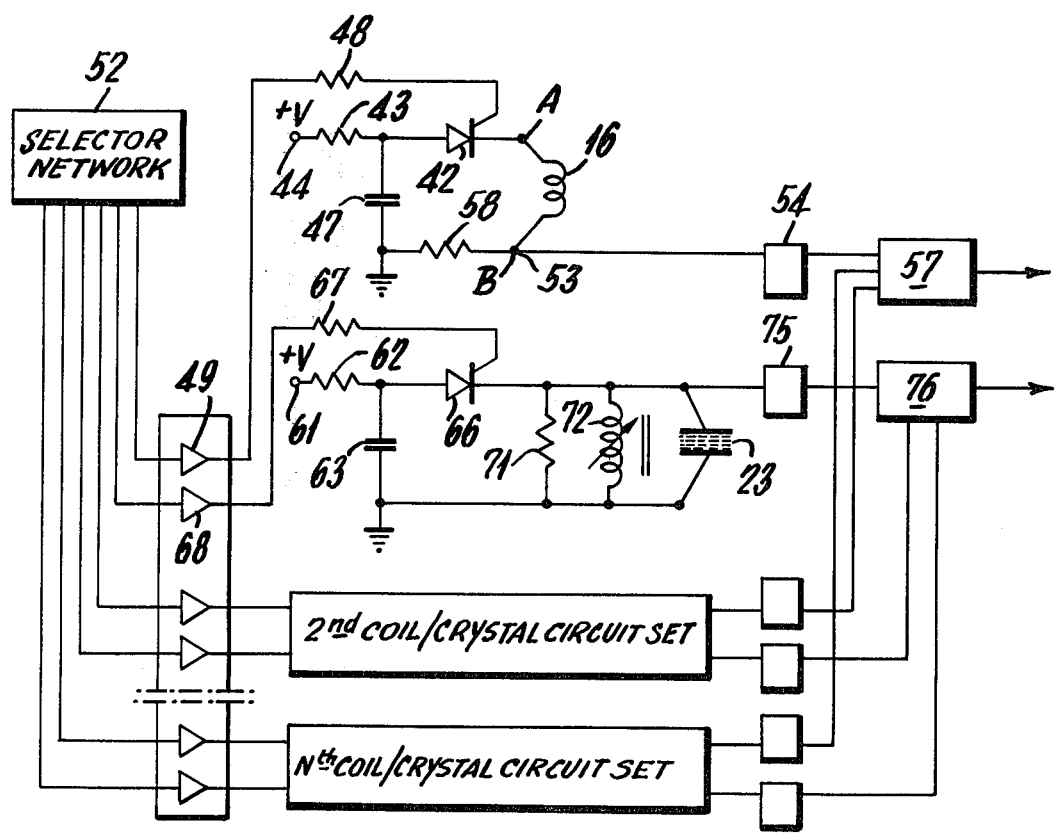
FIG. 2 is a schematic circuit diagram illustrating a system including electrical circuits that might be employed with a plural instrument measuring system for use in a pipe or pipeline.

FIG. 2 illustrates schematic circuits that are suitable for pulsing each of the reluctance coil 16 and the acoustic transducer 23. It may be noted that FIG. 2 also illustrates a plurality of similar circuits which would be employed when the instrument surveying a pipe or pipeline includes a plurality of the instruments 15. These instruments 15 would be positioned around the entire inner periphery of the pipewall 11 in a manner similar to that described in the U.S. Pat. No. 4,022,055.

In connection with each instrument 15, the reluctance coil 16 is pulsed by having a silicon controlled rectifier 42 connected in series therewith. It should be noted that hereafter the common designation SCR will be used to stand for the terms silicon controlled rectifier.

In the circuit illustrated in FIG. 2, the SCR 42 has a circuit connection from its cathode leading to one end of the coil 16. And, its anode is connected via a resistor 43 to a voltage source 44 that is indicated by the plus V caption. There is a capacitor 47 that is charged through the resistor 43 from the source 44. It has one side thereof grounded as indicated.

When the coil 16 is to be pulsed, the SCR 42 will be triggered via a resistor 48 and buffer 49. The buffer 49 acts to pass on a trigger signal which will originate from a selector network 52. Then the signal at a point 53 will be amplified by an amplifier 54 after which it may be transformed by an analog to digital converter 57 if desired. It will be understood that the discharge of capacitor 47 takes place through the SCR 42 and the coil 16 in series therewith on the way back to ground via a resistor 58.

The transducer 23 will be pulsed at or near the time of pulsing of the reluctance coil 16 in order to provide for the distance measurement of the wall 11 from the coil 16. And, the circuit for pulsing the transducer 23 is similar to that for the coil 16. Thus, there is a voltage source terminal 61 with a resistor 62 connected between it and one terminal of a capacitor 63., the other terminal of which is grounded. Another SCR 66 has its control electrode connected via a resistor 67 to another buffer 68. Buffer 68 is connected to the selector network 52 where trigger signal for the transducer 23 also originates.

In this case, when the SCR 66 discharges it goes via a resistor 71 and an inductance 72 both in parallel with the transducer 23. Consequently, this discharge current will pulse the transducer as desired. That acoustic pulse generating signal and the reflected return acoustic signals received by the transducer 23 thereafter, will all be amplified by an amplifier 75 which may have its output connected to an analog/digital converter 76.

It is to be expected that normally the SCR 66 would be triggered first so that the other SCR 42 could be triggered at the time of the arrival of the ultrasonic reflected energies back to the transducer 23. In such manner, a measurement of the distance of the instrument 15 and, particularly, the coil 16 from the wall 11 of the pipe that is being surveyed, will be made at the time when the magnetic reluctance is being measured. Consequently, the accuracy of the reluctance measurement may be verified or a compensating adjustment may be applied to the pulsed magnetic signal from the coil 16.

FIGS. 3, 4, 5 and 6 illustrate pulses that were recorded from an oscilloscope when a reluctance coil and resistor were energized in a laboratory simulation of the FIG. 2 circuit involving the pulsed magnetic coil 16. The trace A in each case represents the applied voltage pulse that is generated when the SCR is triggered and the trace B in each case indicates the IR voltage of the reluctance circuit.

The vertical oscillograph scale in each case, is such that it represents one volt per vertical division, each of which represents one centimeter in the case of the trace A. And, in the case of the trace B in each case, the scale is such that the IR voltage of the reluctance circuit is represented by the vertical divisions (one centimeter) each of which represent two milli-volts per vertical division. The time base of the oscillographs is ten micro seconds per horizontal division which again represent one centimeter each. And, the signal repetition rate is at ten kilo-Hertz.

Figure 3:
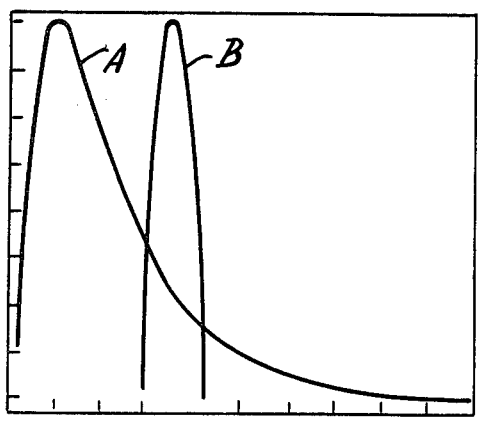
FIGS. 3-6 are illustrations showing oscilloscope traces of signals generated under particular conditions in accordance with the invention.

It is to be noted that the FIG. 3 oscillograph was made with a coil, e.g. coil 16, over a full thickness of material simulating the wall 11. In the actual simulation the full thickness was 0.117 inch.

Figure 4:
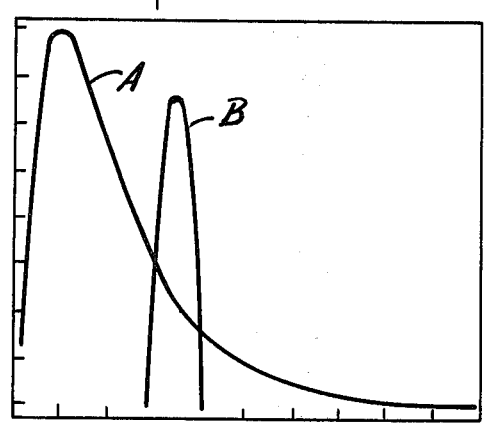

FIG. 4 illustrates another simulation with the same scales and time base. This case employed a depression or pit that was ⅝ inch across and was located on the opposite side of the simulated wall from the coil and had a depth such that the wall was 0.060 inch thick.

Figure 5:
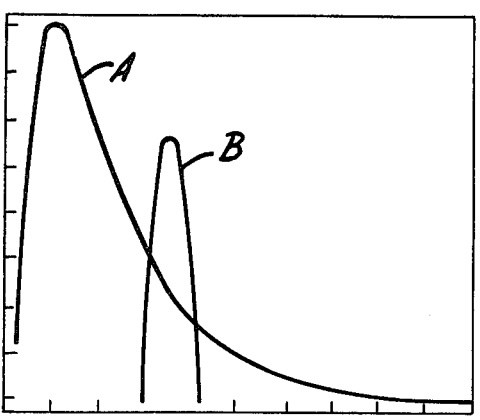
Figure 6:
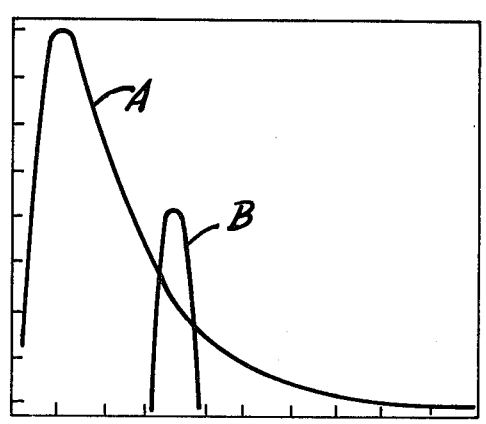

Similarly, FIGS. 5 and 6 illustrate additional simulations which were made with the thickness reduced more in each case. Thus, in FIG. 5 the same scales and time base were employed with the pit being ⅝ inch across and again located on the opposite side of the simulated wall with the depth such that the wall was 0.040 inch thick. And in FIG. 6 the only change was to make the depth of the pit such that the wall was 0.025 inch thick.

It may be noted that in the simulations illustrated in FIGS. 4, 5 and 6, all three were carried out with the coil located on the opposite side of the material being tested from the pit. In other words, the pit was on the other side of the wall from the reluctance coil. As a result, while it was expected that a pit or reduction in thickness of the wall would cause a reduction in the inductance of the coil, the opposite effect was discovered. It appears that a possible explanation for this phenomenon is that the lines of magnetic flux may be concentrated in the thinner metal section which causes an increase in the flux density near the coil center.

Figure 7:
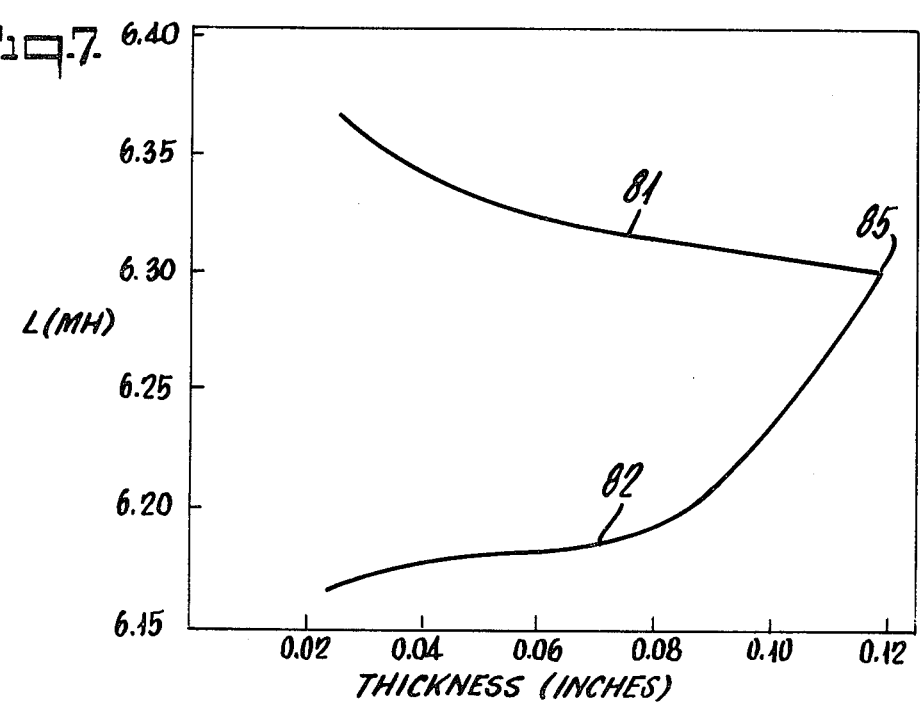
FIG. 7 is a graph showing inductance as the ordinate and the thickness of a wall as the abscissa, of the graph. There are two curves shown, one for the measurement with the wall thickness variation on the same side of the wall as the measuring coil, and the other for the measurement with the thickness variation on the other side from the measuring coil.

Furthermore, it was found that when the pits that were being measured were located on the same side of the material wall as the coil, then the inductance was reduced instead of being increased and thus a manner of determining which side of the wall a pit was located on, has been discovered. This situation is illustrated in FIG. 7 where the graph shows two curves 81 and 82. These were made from measurements of the inductance (on the ordinate of the graph) against the thickness of the plate (on the abscissa of the graph). These curves meet at a point 85 which represents the full thickness of the plate being measured. The curve 81 shows the inductance values when the points that determined the curve were measured with the reduced thicknesses made by a simulated pit in each case, located on the opposite side of the plate from the coil that was employed to make the measurements. On the other hand, the curve 82 shows the values of inductance that were found when the same thickness reductions were tested but with the simulated pit located on the same side as the coil. Therefore, it may be noted that not only may a pit be identified but its location as to whether it is on the same side of the wall being measured or the opposite side thereof, will be indicated by the signals generated.

It will be appreciated that a method according to this invention may be carried out by various and different types of apparatus and the method has the benefits indicated above that make it more accurate and reliable than the previous magnetic surveying methods. Thus, a method, according to this invention, includes the step of applying a pulse of energy to a magnetic reluctance coil that is located with the metallic material in proximity to the coil. And, it includes the step of measuring the inductance of the pulsed coil. The latter is carried out and thereafter, or coextensively therewith, the method includes the step of determining the distance between the pulsed coil and the metallic material. The latter is carried out by employing the transducer and ultrasonic distance measuring technique indicated above.

A mathematical explanation of the magnetic method employed may be clarified by the following explanation. Thus, the self-induced emf $E_s$ is an indication of the quantity of permeable material in the proximity of a pulsed reluctance coil. And, it is related to the permeability, $\mu$, by the following formulae:

$$E_s = \frac{d\phi}{dt} \text{ and } \phi = \frac{Ni}{l/\mu A}$$

where
  $\phi$ = magnetic flux
  i = current
  N = number of turns
  l = length of the flux path (magnetic circuit)
  A = cross-sectional area of the flux path
  $\mu$ = permeability The foregoing equations show that a predictable $d\phi/dt$ requires a known $1/\mu$ ratio and when $\mu$ is very small as in the case for media other than steel, l must be kept small also. The permeabilities of oil, water or gas are several orders of magnitude smaller than that of steel.

While the foregoing explanations have been set forth in considerable detail in accordance with the applicable statutes, this is not to be taken as in any way limiting the invention but merely as being descriptive thereof.

I claim:

1. A combined magnetic and acoustic wall thickness and condition measuring apparatus, comprising in combination
    a reluctance coil having the axis thereof transverse to said wall and adapted for having a small gap between the coil and said wall to include said wall in the magnetic circuit of the coil,
    first circuit means for pulsing said reluctance coil and for determining the permeability of said magnetic circuit,
    an ultrasonic transducer mounted in a fixed position relative to said reluctance coil,
    acoustic reflecting means for directing ultrasonic energy both perpendicular to said wall and at an angle of incidence greater than the critical angle of refraction of said wall, and
    second circuit means for pulsing said transducer and for measuring reflected ultrasonic energy from both said perpendicular and angled energy paths.

2. A combined magnetic and acoustic wall thickness and condition measuring apparatus, comprising in combination
    pulsed magnetic reluctance means for measuring said wall thickness, and
    ultrasonic means for measuring the distance of said magnetic means from said wall and for determining the presence of an anomaly in said wall,
    said ultrasonic means comprising a transducer mounted in a fixed position relative to said magnetic means, and
    means for directing ultrasonic energy both perpendicular to said wall and at an angle of incidence greater than the critical angle of refraction of said wall.

3. A combined apparatus according to claim 2, wherein
    said magnetic means comprises a reluctance coil having the axis thereof transverse to said wall and adapted for having a small gap between the coil and said wall.

4. A combined apparatus according to claim 3, wherein said magnetic means also comprises circuit means for pulsing said reluctance coil and for determining the permeability of the magnetic circuit.

5. A combined apparatus according to claim 4, wherein said ultrasonic means also comprises circuit means for pulsing said transducer and for measuring reflected ultrasonic energy from said wall over both said perpendicular and angled energy paths.

* * * * *